Reissued Apr. 22, 1941 Re. 21,779

UNITED STATES PATENT OFFICE 21,779

NEUTRALIZATION OF ACIDS EXUDING FROM SILICIOUS CEMENTS

Joseph H. Schlesinger, New York, N. Y., assignor to Eagle Chemical Company, New York, N. Y.

No Drawing. Original No. 2,154,413, dated April 11, 1939, Serial No. 49,182, November 11, 1935. Application for reissue October 31, 1939, Serial No. 302,183

4 Claims. (Cl. 32—15)

This invention relates to the neutralization of acids in silicious cements as used in the practice of dentistry.

In common practice silicious cement fillings are prepared by mixing a powdered mass containing kaolin, or a kindred silicate, with a suspending medium, preferably a solution of orthophosphoric or some other of the phosphoric acids, to which oxides of aluminum or calcium have been added. This mixture, when of the proper plastic consistency, is pressed into the thoroughly cleaned and dried tooth cavity.

After the foregoing treatment the patient frequently suffers pain, caused by traces of acid seeping out of the cement and finding its way to the nerve causing a neuralgic irritation, necessitating removal of the filling and renewed treatment of the tooth.

When the silicate powder and the liquid are mixed the fluid phosphoric acid used attacks part of the powder, forming colloidal aluminum phosphate and colloidal silicic acid, consisting of solid silicate particles, imbedded in a matrix of colloidal aluminum phosphate, and a gel of silicic acid, occluding a proportion of free and liquid phosphoric acid.

Kaolin, which is the base of most silicious cement preparations on the market, often contains fluorides of aluminum which, in contact with phosphoric acid, will yield hydrofluoric acid; likewise traces of arsenic may be found in kaolin which may give origin to arsenious acid. All these acids, even in minute quantities, when they exude from the cement and come into contact with the tissues or the structure of the tooth will cause pain and eventually devitalize the pulp of the tooth.

One object is to neutralize any free acids which may exude from the filling while in the process of cementation. This object relates to the inner surface of the cement plug as well as to the outer surface.

A further feature is to prepare and impregnate the surface of the cavity into which the filling is to be pressed with an alkaline medium to counteract any acid which may come from the filling, whether or not an intermediate lining be used, while a concurrent object is to simultaneously neutralize and absorb any acidulous moisture which may exude from the outer surface of the filling.

A further salient feature of this invention is the use of an absorbing and neutralizing means which can be readily applied and used in connection with all filling material which develops free and potentially injurious acids while solidifying.

These objects and advantages will become apparent from the following detailed disclosure.

An important step of the filling process comprises the impregnation of the inner surface of the cleaned cavity with a liquid dilute alkali.

The process is also applicable in cases where silicate cements in whole or part are merely used as a cementing medium, as for examples for gold and porcelain crowns, inlays, and other dental restorations.

In operation, after the cavity in the tooth is cleaned and dried, its inside should be thoroughly daubed or swabbed with a dilute alkaline solution (hydroxides of the alkali metals, sodium carbonate or any other suitable alkali), and given time to dry. The tooth cavity should be protected from moisture until the filling is inserted.

The leading principle of the invention is to overcome the irritating effect of silicious cement fillings of live teeth. Alkalizing, neutralizing and absorption of surplus acidic moisture are the contributing and dominating factors of the process.

Having described the invention, what is claimed as new and sought to secure by Letters Patent, is:

1. In the process of filling dental cavities with silicious cement containing a mineral acid, the steps consisting of alkalizing the interior surface of the cavity with an absorbable liquid alkali, prior to filling to prevent injury to live pulp, filling the cavity with the cement and neutralizing the entered filling by an exterior application of alkaline media.

2. In the process of using silicious cement when mixed with mineral acids as a cementing medium to retain dental restorations in adjusted position relative to a tooth prepared therefor, the step which consists of treating the tooth surfaces to receive the restoration with a liquid absorbable alkali.

3. A composition of matter for treating a tooth cavity to receive an acid-exuding cement filling, the said composition comprising an absorbable solution of alkali adapted to alkalize the field of operation, neutralize exuded acid, and reduce the irritating effect of the cement.

4. In the filling of dental cavities with cement containing a mineral acid, the method which comprises the pre-treatment of the cavity with an aqueous solution of an alkali, drying the applied solution to cause evaporation of water and leave substantially dry alkali over the inside of the cavity, filling the pretreated cavity with the said cement, and, by the alkali applied in the pretreatment, neutralizing acid exuded by the said cement at positions of contact of the cement with the tooth structure and reducing the irritating effect of the cement.

JOSEPH H. SCHLESINGER.